(12) United States Patent
Baba et al.

(10) Patent No.: US 11,504,025 B2
(45) Date of Patent: Nov. 22, 2022

(54) MASK

(71) Applicant: NIHON KOHDEN CORPORATION, Tokyo (JP)

(72) Inventors: Yuya Baba, Tokyo (JP); Isao Matsubara, Tokyo (JP); Masayuki Inoue, Tokyo (JP); Kenichiro Kabumoto, Tokyo (JP); Fumihiko Takatori, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 314 days.

(21) Appl. No.: 15/895,714

(22) Filed: Feb. 13, 2018

(65) Prior Publication Data

US 2018/0228400 A1 Aug. 16, 2018

(30) Foreign Application Priority Data

Feb. 13, 2017 (JP) .............................. JP2017-024394

(51) Int. Cl.
*A61B 5/097* (2006.01)
*A61B 5/00* (2006.01)
(Continued)

(52) U.S. Cl.
CPC ............ *A61B 5/097* (2013.01); *A61B 5/0836* (2013.01); *A61B 5/682* (2013.01); *A61B 5/6803* (2013.01);
(Continued)

(58) Field of Classification Search
CPC .............. A61M 16/06; A61M 2205/33; A61M 2205/3327; A61M 2202/0225;
(Continued)

(56) References Cited

U.S. PATENT DOCUMENTS 7,841,988 B2 * 11/2010 Yamamori ............ A61M 16/06
600/532
8,915,861 B2 * 12/2014 Yamamori ........... A61B 5/0836
600/532
(Continued)

FOREIGN PATENT DOCUMENTS

EP 2275031 A1 1/2011
EP 2589404 A1 5/2013
(Continued)

OTHER PUBLICATIONS

Translation of JP 62092802. Accessed from JPlatPat on Mar. 23, 2021. (Year: 1987).*
(Continued)

*Primary Examiner* — Valerie L Woodward
*Assistant Examiner* — Paige Kathleen Bugg
(74) *Attorney, Agent, or Firm* — Dorsey & Whitney LLP

(57) ABSTRACT

To provide a mask capable of reducing a load of a patient while suppressing lowering of accuracy at which a subject's exhaled air is measured. A mask to be put on a subject's face includes a mask body portion demarcating an internal space in a state of covering part of the subject's face and a cup-shaped nasal cup covering a subject's nose in a state of being arranged inside the internal space, in which the nasal cup includes a first wall portion covering the subject's nose, a second wall portion arranged under the subject's nostrils, and an exhaled air discharge portion guiding an exhaled air from the subject's nose to an exhaled air sensor, and at least part of the exhaled air from the subject's nose is guided toward the exhaled air discharge portion by the second guide portion in a state where the nasal cup covers the subject's nose.

27 Claims, 18 Drawing Sheets

(51) Int. Cl.
*A61M 16/06* (2006.01)
*A61B 5/083* (2006.01)
*A61M 16/08* (2006.01)
*A61B 5/08* (2006.01)
*A61B 5/087* (2006.01)

(52) U.S. Cl.
CPC ........... *A61B 5/6819* (2013.01); *A61M 16/06* (2013.01); *A61M 16/0605* (2014.02); *A61M 16/085* (2014.02); *A61B 5/082* (2013.01); *A61B 5/0873* (2013.01); *A61M 2205/3313* (2013.01); *A61M 2230/432* (2013.01)

(58) Field of Classification Search
CPC ...... A61M 16/0683; A61M 2201/0618; A61B 5/00; A61B 5/08; A61B 5/083; A61B 5/087; A61B 5/097
USPC ........... 128/203.12, 204.22, 205.11, 206.24, 128/205.24, 206.28, 205.25, 206.25
See application file for complete search history.

(56) References Cited

U.S. PATENT DOCUMENTS

| | | | | |
|---|---|---|---|---|
| 9,566,018 | B2* | 2/2017 | Yamamori | ........... A61B 5/0836 |
| 9,775,541 | B2* | 10/2017 | Inoue | ..................... A61B 5/097 |
| 10,413,697 | B2* | 9/2019 | Takatori | ................ A61M 16/06 |
| 2006/0196510 | A1* | 9/2006 | McDonald | ......... A61M 16/0611 |
| | | | | 128/206.21 |
| 2007/0113847 | A1* | 5/2007 | Acker | ................... A61M 16/00 |
| | | | | 128/204.18 |
| 2008/0078396 | A1* | 4/2008 | Janbakhsh | ............ A61M 16/06 |
| | | | | 128/205.25 |
| 2008/0196715 | A1 | 8/2008 | Yamamori | |
| 2008/0319334 | A1 | 12/2008 | Yamamori | |
| 2010/0122704 | A1 | 5/2010 | Moenning, Jr. | |
| 2010/0122705 | A1 | 5/2010 | Moenning, Jr. | |
| 2010/0122706 | A1 | 5/2010 | Moenning, Jr. | |
| 2011/0015534 | A1* | 1/2011 | Yamamori | ........... A61B 5/0836 |
| | | | | 600/532 |
| 2014/0083425 | A1 | 3/2014 | Moenning, Jr. | |
| 2014/0330154 | A1 | 11/2014 | Haveri | |
| 2015/0099986 | A1* | 4/2015 | Inoue | ....................... A62B 7/10 |
| | | | | 600/479 |
| 2017/0196512 | A1 | 7/2017 | Inoue | |
| 2018/0043121 | A1* | 2/2018 | Goulitski | .......... A61M 16/0666 |

FOREIGN PATENT DOCUMENTS

| | | | |
|---|---|---|---|
| EP | 2859845 | A1 | 4/2015 |
| JP | 62-092802 | U | 6/1987 |
| JP | 62092802 | U * | 6/1987 |
| JP | 2008200061 | A | 9/2008 |
| JP | 2011036643 | A | 2/2011 |
| JP | 2011102747 | A | 5/2011 |
| JP | 2012509148 | A | 4/2012 |
| JP | 2015073751 | A | 4/2015 |
| WO | 2016201358 | A1 | 12/2016 |

OTHER PUBLICATIONS

Extended European Search Report received in European Application No. 18154383.6 dated Jul. 10, 2018.

Office Action for EP Application No. 18154383.6, dated Jan. 2, 2020.

English translation of Office Action for JP Application No. 2017-024394, dated Nov. 24, 2020.

* cited by examiner

MASK

CROSS-REFERENCE TO RELATED APPLICATIONS

This application claims the benefit under 35 U.S.C. § 119 of the earlier filing date of Japanese application 2017-024394 filed Feb. 13, 2017. The priority Japanese application is hereby incorporated by reference in its entirety for any purpose.

BACKGROUND

A mask described in JP-A-2011-036643 (Patent Document 1) has been known as a mask applicable to, for example, apparatuses for a CPAP (Continuous Positive Airway Pressure) method or an NPPV (Non-invasive Positive Pressure Ventilation) method used for treatment of patients with a sleep apnea syndrome or a respiratory failure.

In the mask described in Patent Document 1, an exhaled air of a subject reaches an airway case through a nasal tube inserted into nostrils of the subject and is led to a detector of an exhaled gas concentration sensor. According to the structure, the exhaled air from a nose is not diluted by oxygen flowing from an inlet of the mask, therefore, the gas concentration in the exhaled air of the subject can be accurately measured under positive pressure ventilation which has been difficult in the past.

As the nasal tube is used in the structure of Patent Document 1, a load of the subject is not small. However, the exhaled air of the subject is diluted by oxygen flowing from the inlet of the mask without using the nasal tube, therefore, it is difficult to accurately measure a state of the exhaled air

SUMMARY

An object of the present disclosure is to provide a mask capable of reducing a load of a patient while suppressing lowering of accuracy at which an exhaled air of a subject is measured.

A mask according to the present disclosure is a mask to be put on a face of a subject, which includes a mask body portion demarcating an internal space in a state of covering part of the face of the subject and a cup-shaped nasal cup covering a nose of the subject in a state of being arranged inside the internal space, in which the nasal cup has a first wall portion covering the nose of the subject, a second wall portion arranged under nostrils of the subject, and an exhaled air discharge portion guiding an exhaled air from the nose of the subject to an exhaled air sensor, and at least part of the exhaled air from the nose of the subject is guided toward the exhaled air discharge portion by the second wall portion in a state where the nasal cup covers the nose of the subject.

According to the above structure, it is possible to suppress that the exhaled air from the nose of the subject is diluted by oxygen flowing from an inlet of the mask by the first wall portion and the second wall portion of the nasal cup. As at least part of the exhaled air from the nose of the subject is guided toward the exhaled air discharged portion by the second wall portion, the exhaled air can be positively guided to the detection space of the exhaled air sensor even when the nose tube having a high load for the subject is not used. As described above, it is possible to provide a mask capable of reducing the load of the patient while suppressing lowering of accuracy at which the exhaled air of the subject is measured according to the above structure.

According to the present disclosure, it is possible to provide the mask capable of reducing the load of the patient while suppressing lowering of accuracy at which the exhaled air of the subject is measured.

DETAILED DESCRIPTION

Hereinafter, a mask according to embodiments of the present disclosure will be explained with reference to the drawings.

First Embodiment

Figure 1:
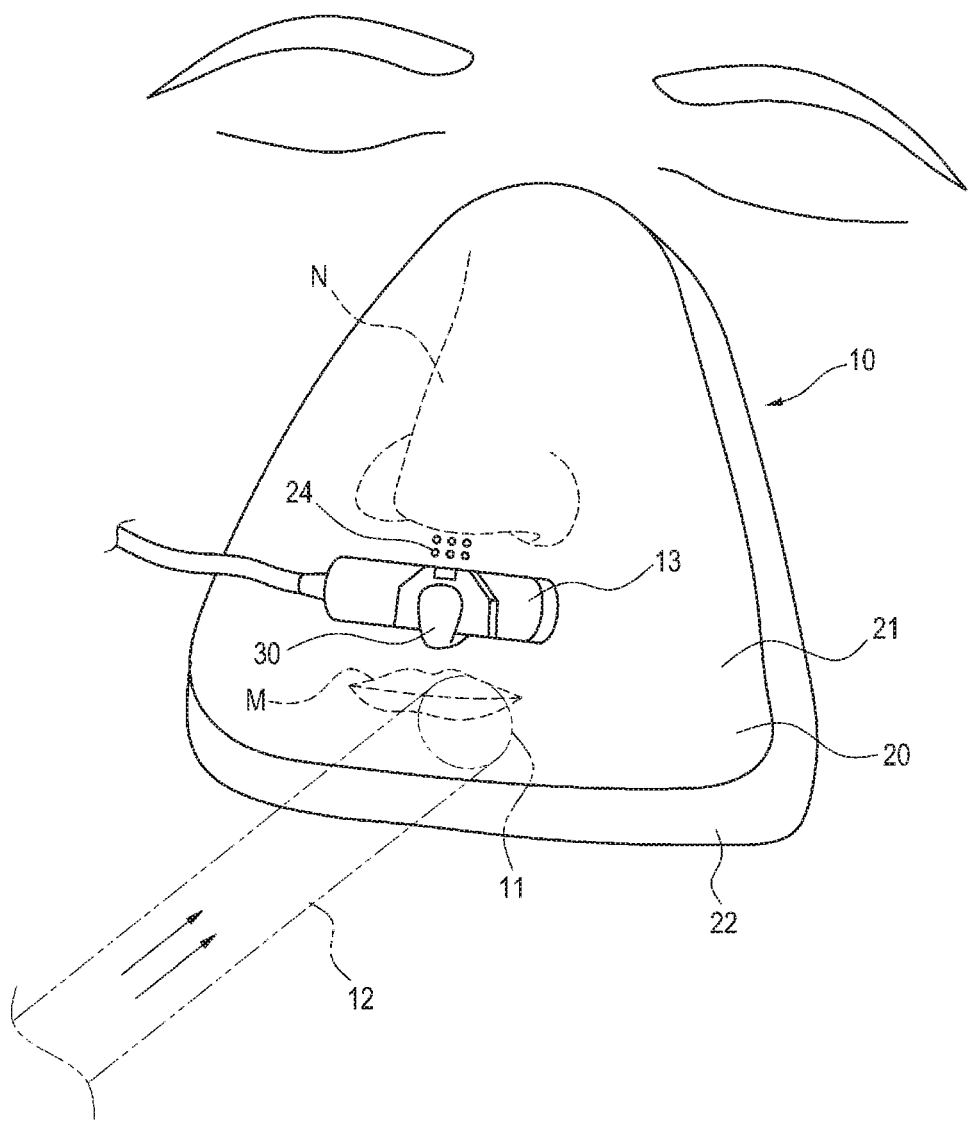
FIG. 1 is a perspective view showing a state where a mask according to a first embodiment of the present disclosure is put on a face of a subject.
Figure 2:
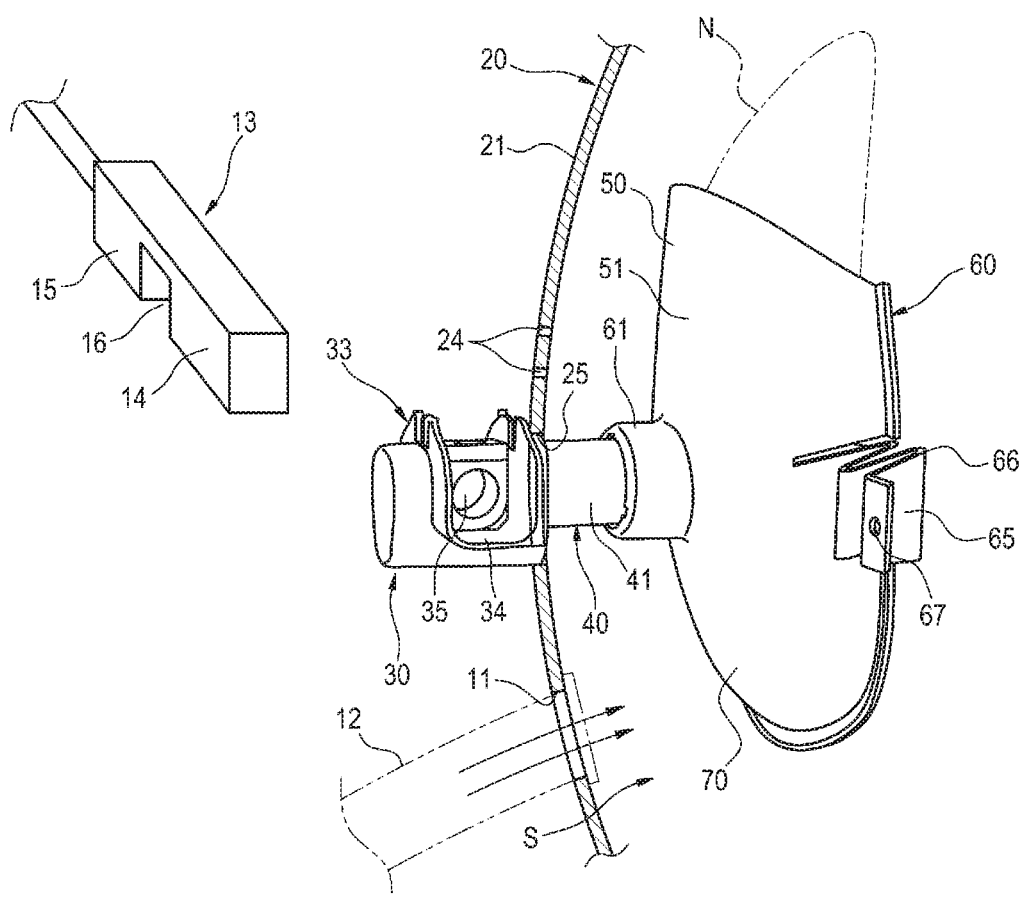
FIG. 2 is a perspective view in a cross section of a mask body portion showing the state where the mask according to the first embodiment of the present disclosure is put on the face of the subject.
Figure 3:
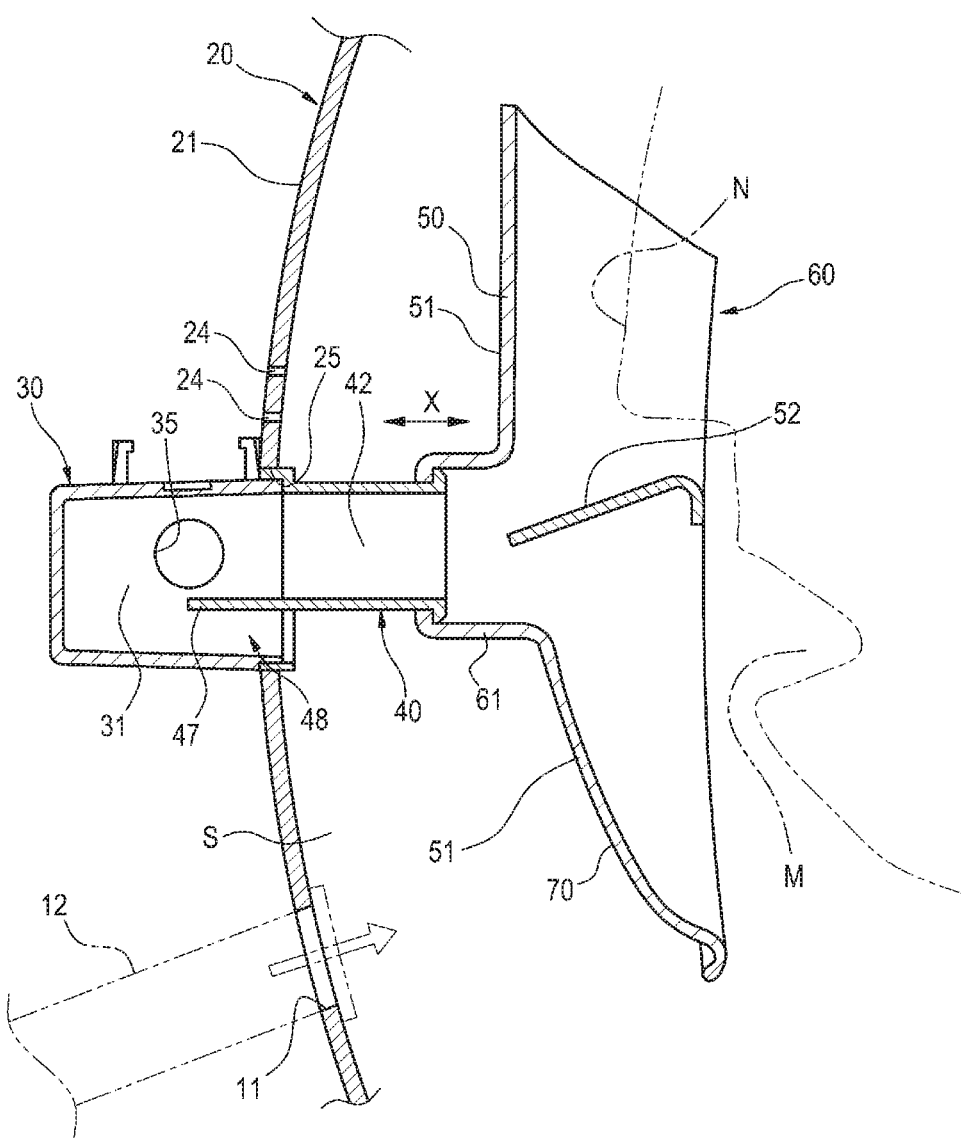
FIG. 3 is a cross-sectional view of the mask according to the first embodiment of the present disclosure.

As shown in FIG. 1 to FIG. 3, a mask 10 according to the embodiment is provided with a mask body portion 20 and a nasal cup 50. The mask 10 is a mask applicable to, for example, apparatuses for a CPAP (Continuous Positive Airway Pressure) method or an NPPV (Non-invasive Positive Pressure Ventilation) method used for treatment of patients with a sleep apnea syndrome or a respiratory failure, which is put on a face of a subject.

The mask body portion 20 demarcates an internal space S in a state where part of the face of the subject is covered. Specifically, the mask body portion 20 is put on the subject so as to cover a nose N and a mouth M on the face of the subject. The nasal cup 50 is formed in a cup shape and arranged inside the internal space S demarcated by the mask body portion 20. The nasal cup 50 is attached to the face of the subject inside the internal space S so as to cover the nose N and the mouth M of the subject.

The mask body portion 20 includes a covering portion 21 and an attachment portion 22. The covering portion 21 is made of resin such as a vinyl chloride resin and is formed in a concave shape entirely expanding toward the front of the face so as to cover the nose N and the mouth M. The attachment portion 22 is provided at a peripheral edge of the covering portion 21. The attachment portion 22 is made of a material which can be elastically deformed such as rubber and silicon, which is integrally formed with the covering portion 21. Accordingly, the mask body portion 20 is attached to the face of the subject, and the attachment portion 22 is closed to the face of the subject.

An opening 25 is formed in the mask body portion 20. The opening 25 is formed in the vicinity of a portion between the nose N and the mouth M of the subject putting on the mask body portion 20. A ventilation member 30 is attached and connected to the opening 25 from an outer surface side of the mask body portion 20, and an exhaled air sensor 13 is supported at the ventilation member 30.

The exhaled air sensor 13 is a sensor measuring a carbon dioxide concentration in an exhaled air. The exhaled air sensor 13 includes, for example, a light emitting portion 14 having a light emitting device formed of an infrared light source and a light receiving portion 15 having a light receiving device formed of, for example, a photodiode. The light emitting portion 14 and the light receiving portion 15 are connected to each other with a gap, and the gap between the light emitting portion 14 and the light receiving portion 15 is a detection space 16. The light emitting portion 14 is provided with the light emitting device on a surface facing the light receiving portion 15 and the light receiving portion 15 is provided with the light receiving device on a surface facing the light emitting portion 14, therefore, the light emitting device and the light receiving device are arranged to face each other on the same optical axis.

In the mask body portion 20, holes 24 are provided above the opening 25. In the example, 6 holes 24 are provided and the internal space S communicates with the outside through these holes 24. It is sufficient that at least one hole 24 is formed.

An oxygen supply pipe 12 is connected to the mask body portion 20. The oxygen supply pipe 12 is a pipe for supplying oxygen into the internal space 5, which is connected to an inlet 11 in the vicinity of the mouth M of the subject putting on the mask body portion 20. Then, the internal space S of the mask 10 is under the positive pressure ventilation by supplying oxygen from the oxygen supply pipe 12.

The nasal cup 50 forms an exhaled air collection cup 60 by being formed integrally with a mouth cup 70. The nasal cup 50 leads the exhaled air from the nose N of the subject to the exhaled air sensor 13 and the mouth cup 70 leads the exhaled air from the mouth M of the subject to the exhaled air sensor 13.

Figure 4:
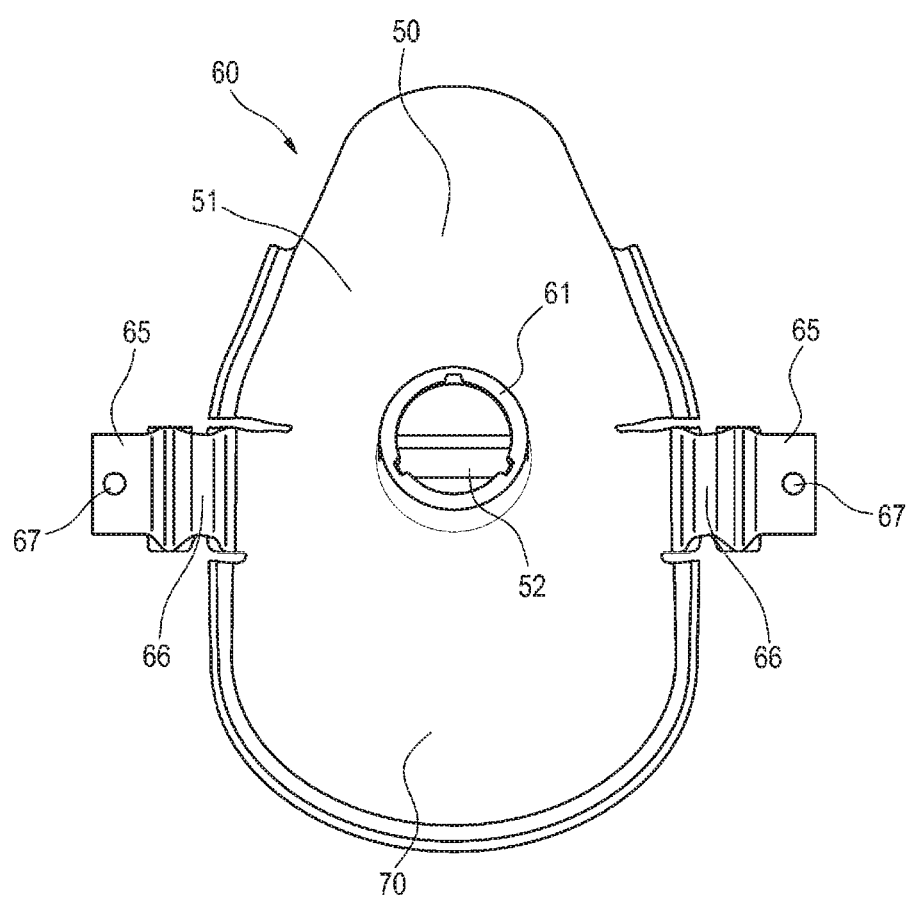
FIG. 4 is a front view of an exhaled air collection cup.
Figure 5:
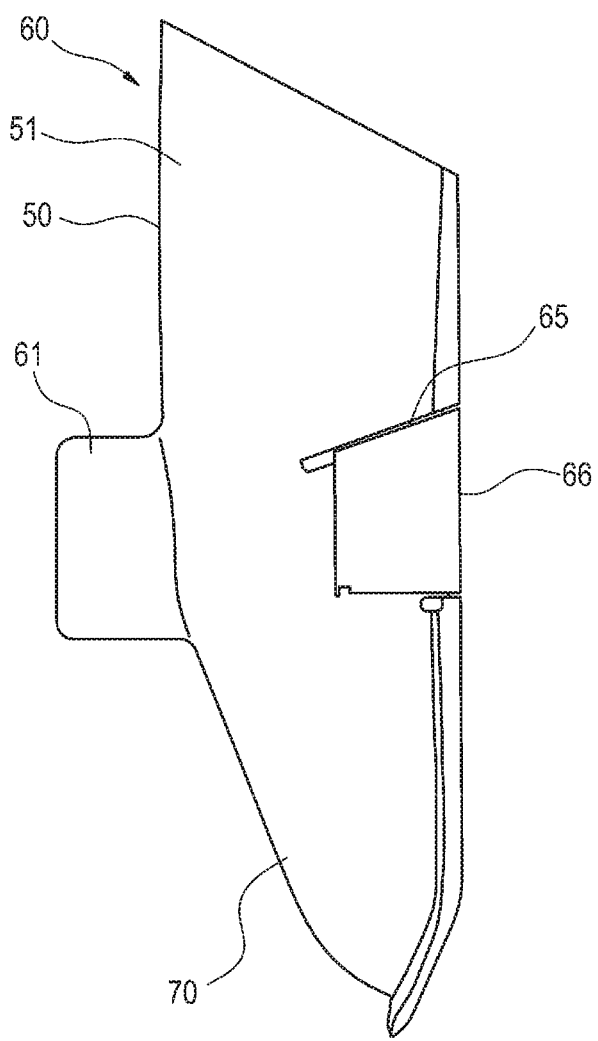
FIG. 5 is a side view of the exhaled air collection cup.
Figure 6:
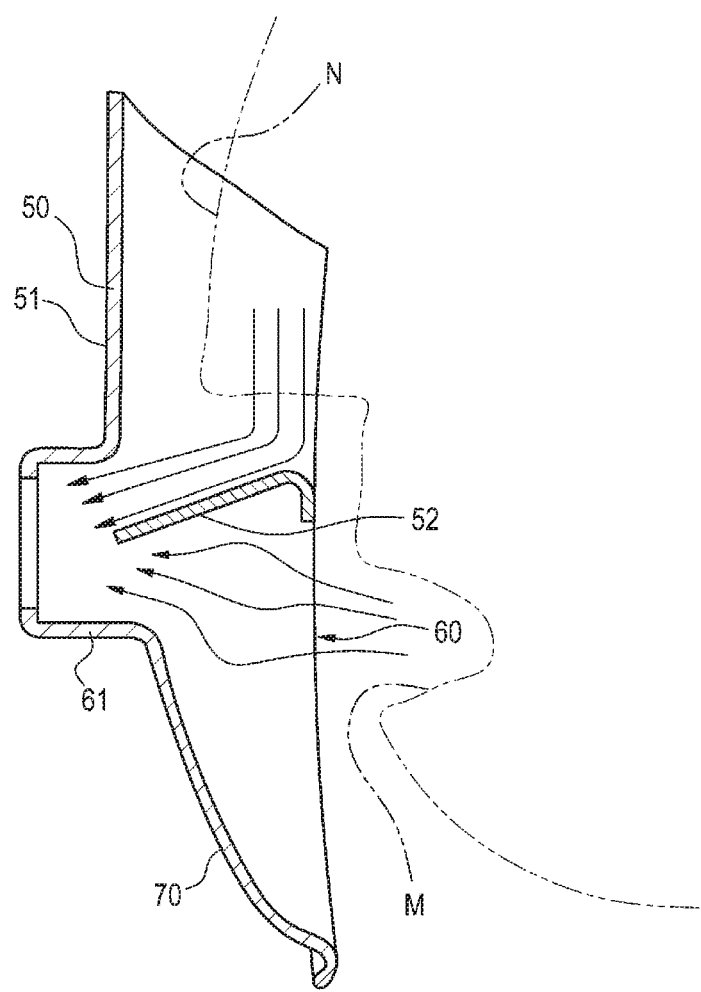
FIG. 6 is a cross-sectional view of the exhaled air collection cup.
Figure 7:
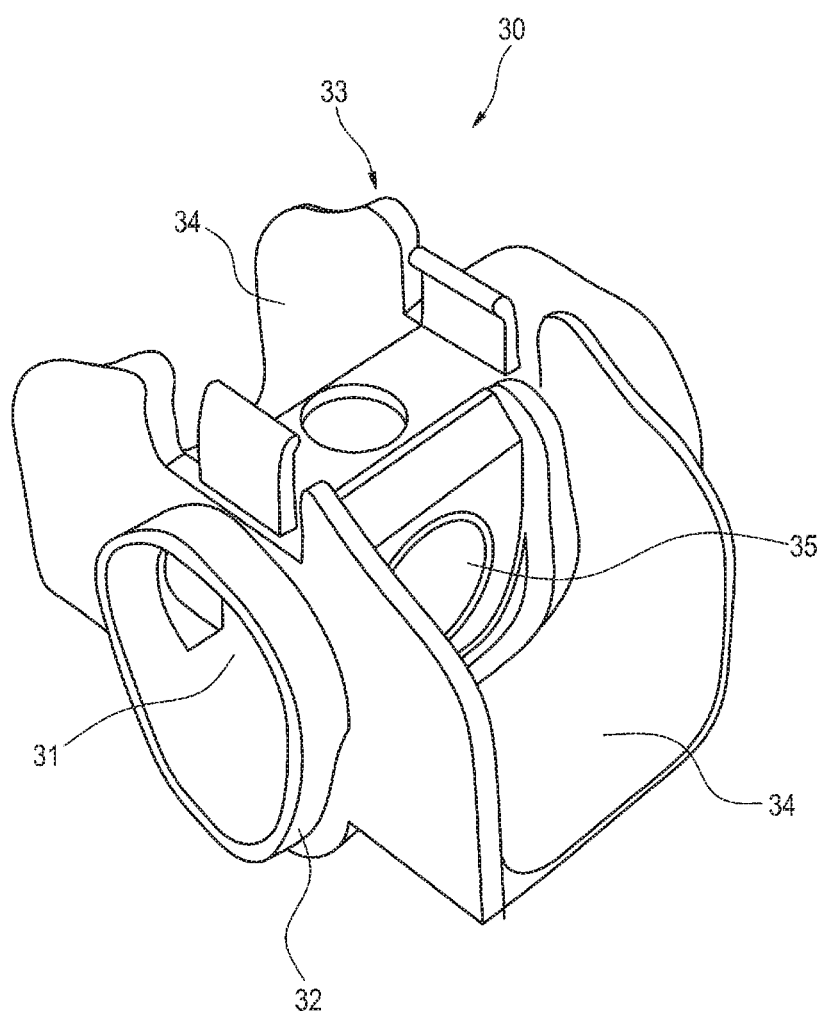
FIG. 7 is a perspective view seen from a rear side of a ventilation member.
Figure 8:
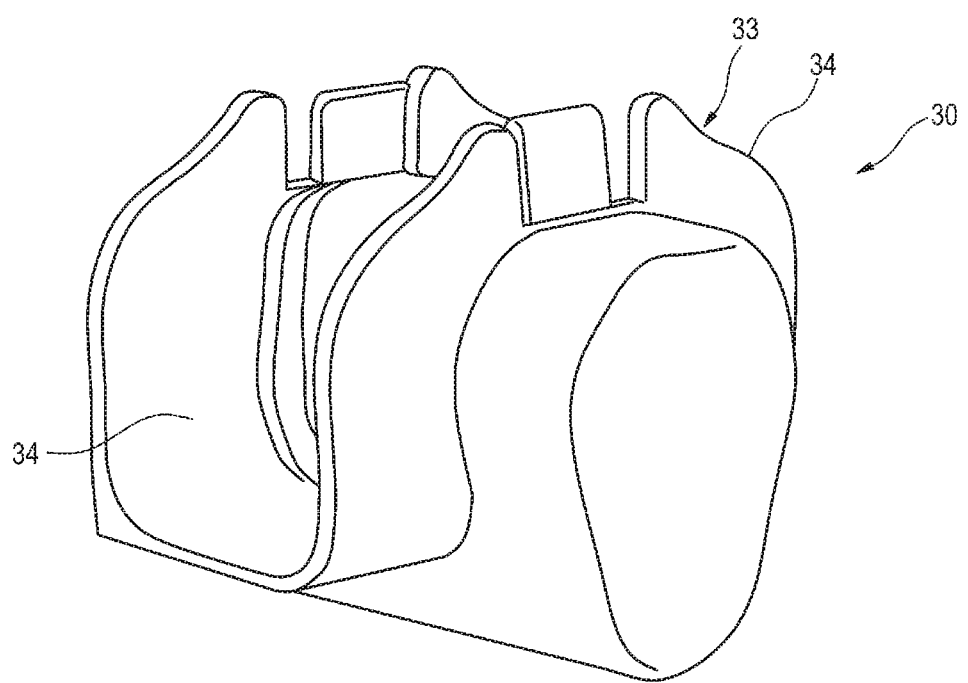
FIG. 8 is a perspective view seen from a front side of the ventilation member.
Figure 9:
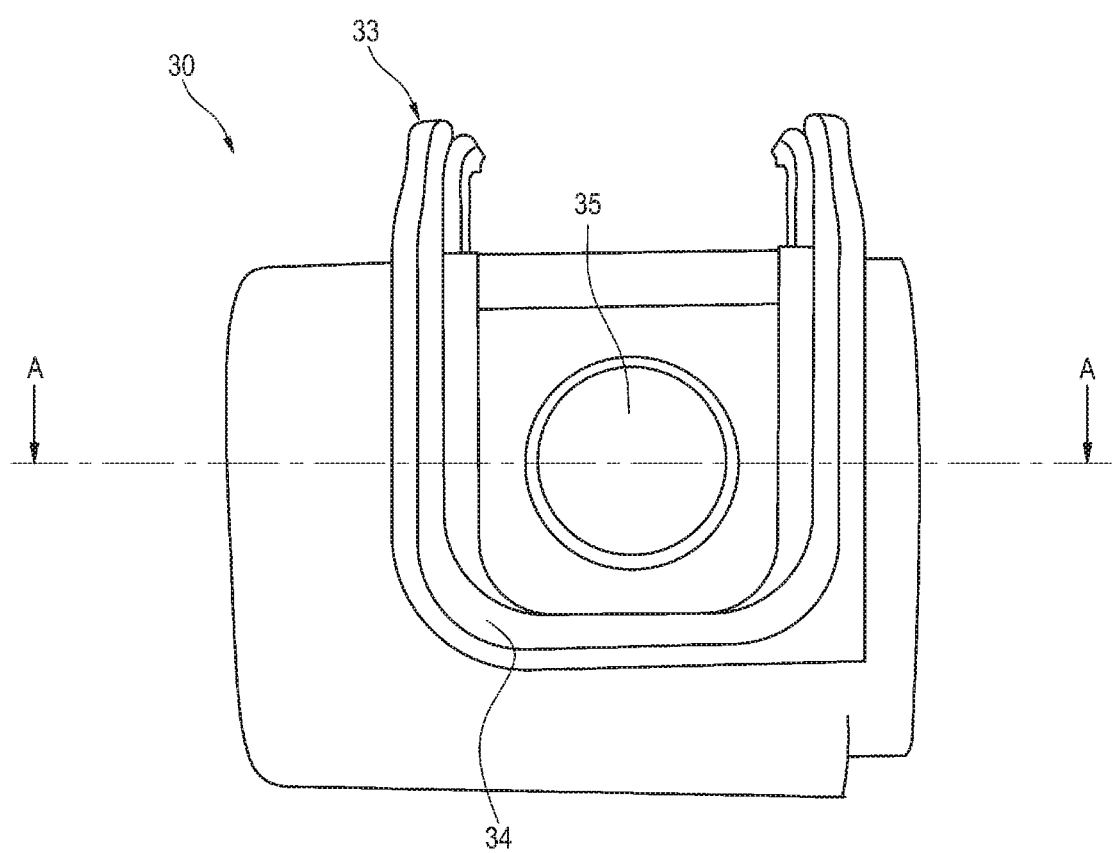
FIG. 9 is a side view of the ventilation member.
Figure 10:
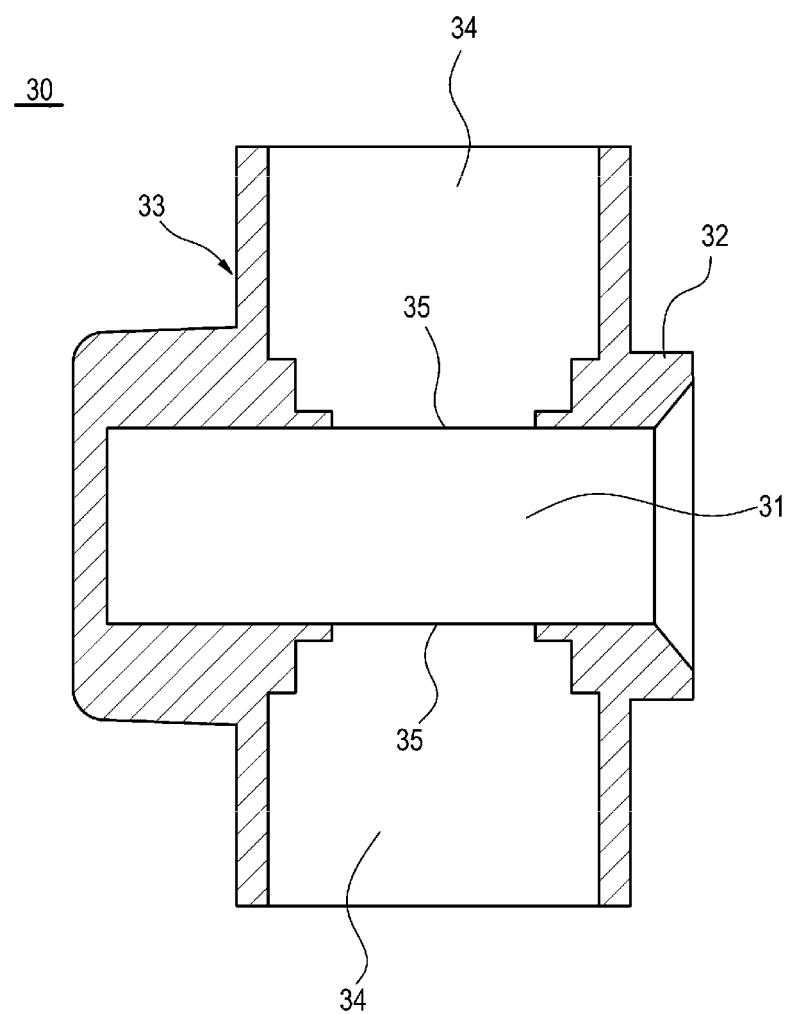
FIG. 10 is a cross-sectional view taken along A-A of FIG. 9.

As shown in FIG. 4 to FIG. 6, the nasal cup 50 includes a first wall portion 51 covering the nose N of the subject and a second wall portion 52 arranged under nostrils of the subject. The first wall portion 51 is formed in a concave shape expanding to the front and is extended downward beyond the second wall portion 52. The mouth cup 70 includes the first wall portion 51 extended downward and the second wall portion 52 arranged under the nostrils of the subject. The nasal cup 50 and mouth cup 70 are partitioned into respective internal spaces by the second wall portion 52.

The nasal cup 50 is arranged with a gap so that an upper part does not closely contact the nose N of the subject. The nasal cup 50 may have a shape closely contacting the nose of the subject.

The exhaled air collection cup 60 having the nasal cup 50 and the mouth cup 70 has an exhaled air discharge portion 61. The exhaled air discharge portion 61 is formed integrally with the first wall portion 51, which is formed in a tubular portion protruding to the front. The exhaled air discharge portion 61 in the embodiment is provided at an interface portion between the nasal cup 50 and the mouth cup 70. The exhaled air discharge portion 61 is connected to the ventilation member 30 through a relay portion 40. At least part of the exhaled air from the nose N of the subject is guided by the second wall portion 52 and fed into the exhaled air discharge portion 61. At least part of the exhaled air from the mouth M of the subject is guided by the second wall portion 52 and fed into the exhaled air discharge portion 61. The exhaled air from the nose N and the mouth M fed into the exhaled air discharge portion 61 is guided to the ventilation member 30 where the exhaled air sensor 13 is supported through the relay member 40.

The exhaled air collection cup 60 having the nasal cup 50 and the mouth cup 70 has fitting portions 65 at both ends thereof. These fitting portions 65 are formed in a band shape respectively extending right and left, which are formed integrally with the exhaled air collection cup 60. Each fitting portion 65 has a bellows-shaped elongation/contraction portion 66 alternately folded in a wave shape, which can be elongated and contracted at the elongation/contraction portion 66. Fitting holes 67 are formed at end portions of the fitting portions 65, fitting pins (not shown) formed on both sides of the mask body portion 20 are inserted into the fitting holes 67, thereby connecting the fitting portions 65 to the mask body portion 20. Accordingly, the exhaled air collection cup 60 having the nasal cup 50 and the mouth cup 70 is attached to the mask body portion 20. The exhaled air collection cup 60 including the nasal cup 50 and the mouth cup 70 attached to the mask body portion 20 by the fitting portions 65 can adjust the position with respect to the mask body portion 20 as the elongation/contraction portions 66 of the fitting portions 65 having the bellows shape can be elongated and contracted. For example, the exhaled air collection cup 60 can adjust the position in directions coming close to and away from the mask body portion 20 (directions of an arrow X in FIG. 3) easily.

As shown in FIG. 7 to FIG. 10, the ventilation member 30 is formed into a bottomed tubular shape having an exhaled air flow path 31 with one opened end and the other blocked end. One end side of the ventilation member 30 where the exhaled air flow path 31 opens is a connecting portion 32 formed in a ring shape protruding downward, and the connecting portion 32 is fitted to the opening 25 of the mask body portion 20. The ventilation member 30 can be attachable/detachable with respect to the mask body portion 20 by inserting and extracting the ventilation member 30 with respect to the opening 25.

The ventilation member 30 has a supporting portion 33. The supporting portion 33 supports the exhaled air sensor 13. The supporting portion 33 includes engaging concave portions 34 formed on right and left both sides with the exhaled air flow path 31 interposed therebetween. Each engaging concave portion 34 is formed in a U-shape with an upper side opened. Detection windows 35 communicating with the exhaled air flow path 31 are formed inside respective engaging concave portions 34.

The exhaled air sensor 13 with the detection space 16 facing downward is attached to the supporting portion 33 of the ventilation member 30 from an upper direction. In the exhaled air sensor 13 attached to the supporting portion 33, the ventilation member 30 is fitted into the detection space 16, and the light emitting portion 14 and the light receiving portion 15 are fitted into the engaging concave portions 34. The light emitting device of the light emitting portion 14 and the light receiving device of the light receiving portion 15 are arranged inside the detection windows 35 so that optical axes of the light emitting device and the light receiving device pass through the exhaled air flow path 31. Accordingly, the exhaled air sensor 13 can measure carbon dioxide in the exhaled air of the subject flowing in the exhaled air flow path 31.

Figure 11:
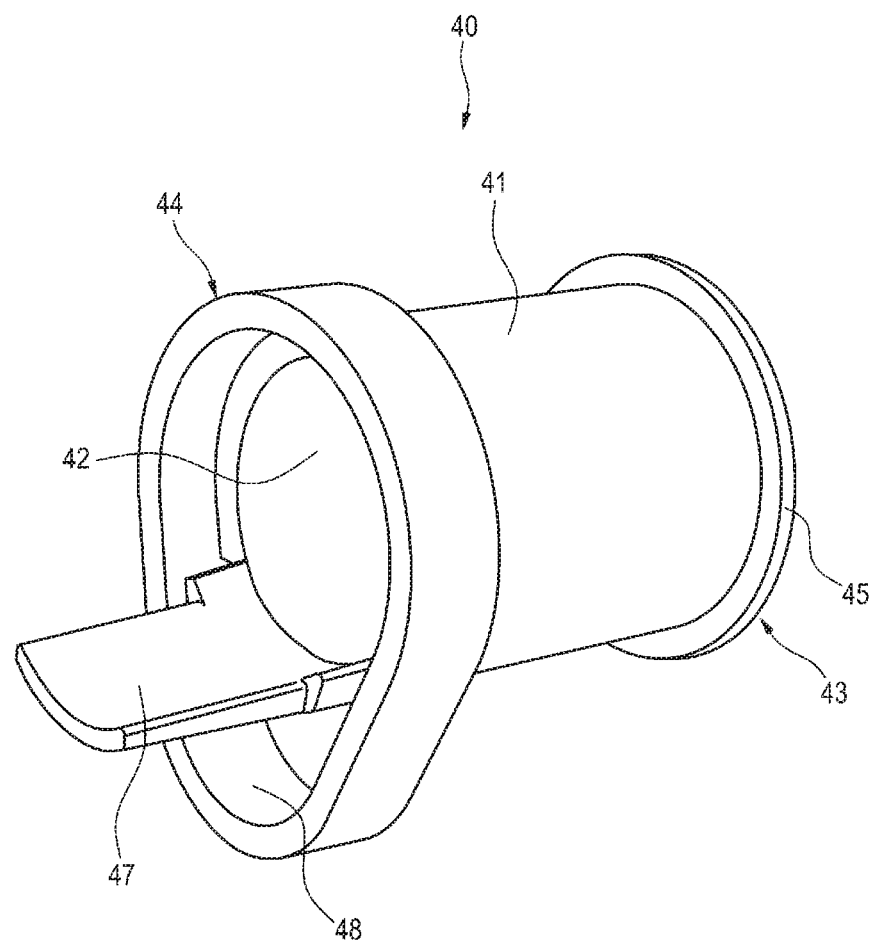
FIG. 11 is a perspective view of a relay member.

As shown in FIG. 11, the relay member 40 has a cylindrical portion 41 formed in a cylindrical shape, and an inside of the cylindrical portion 41 is made to be a first flow path 42. In the cylindrical portion 41, one end side is an inflow-side joining portion 43 and the other end side is an outflow-side joining portion 44. An engaging flange portion 45 projecting to an outer peripheral side is formed in the inflow-side joining portion 43. The inflow-side joining portion 43 is inserted into the exhaled air discharge portion 61 of the exhaled air collection cup 60 provided with the nasal cup 50 and mouth cup 70 and joined to the exhaled air discharge portion 61. Then, the inflow-side joining portion 43 is prevented from falling off by the engaging flange portion 45 being engaged to an edge portion of the exhaled air discharge portion 61. The outflow-side joining portion 44 is formed in a ring shape protruding downward, and the connecting portion of the ventilation member 30 inserted into the opening 25 of the mask body portion 20 is fitted to the outflow-side joining portion 44.

In the relay member 40, a relay wall portion 47 is formed on a connection side with respect to the ventilation member 30. The relay wall portion 47 protrudes from a lower part of the cylindrical portion 41. The relay member 40 has a second flow path 48 below the relay wall portion 47. The second flow path 48 is formed by the cylindrical portion 41 and the connection portion 32.

The exhaled air of the subject flows inside the first flow path 42 of the relay member 40 from the exhaled air discharge portion 61 toward the ventilation member 30. The exhaled air of the subject flows inside the second flow path 48 of the relay member 40 from the ventilation member 30 toward the internal space S. As described above, the first flow path 42 and the second flow path 48 are arranged in parallel to each other and the exhaled air flows in opposite directions to each other.

Next, flows of the exhaled air and so on in a state where the mask 10 having the above structure is put on the face of the subject will be explained.

Figure 12:
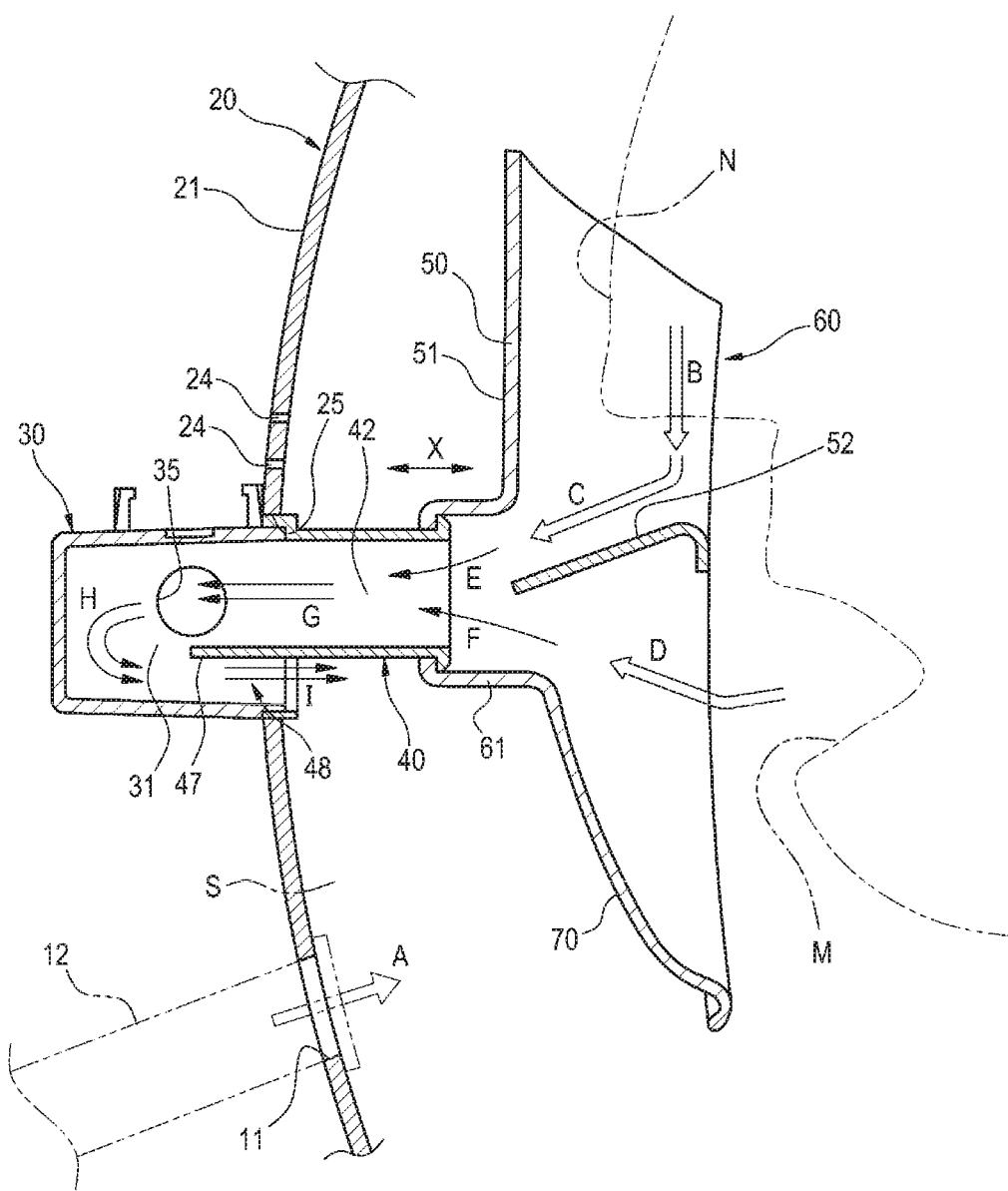
FIG. 12 is a cross-sectional view of the mask showing flows of an exhaled air and so on in the state where the mask is put on the face of the subject.

As shown in FIG. 12, in the mask 10 put on the face of the subject, oxygen is fed into the internal space S formed by the mask body portion 20 from the oxygen supply pipe 12 (see an arrow A in FIG. 12).

The exhaled air from the nose N of the subject is guided toward the exhaled air discharge portion 61 by the second wall portion 52 of the nose cup 50 (see arrows B and C in FIG. 12). The exhaled air from the mouth M of the subject is also guided to the exhaled air discharge portion 61 (see an arrow D in FIG. 12). Then, exhaled airs from the nose N and the mouth M are joined together in the exhaled air discharge portion 61 (see arrows E and F) and are fed to the exhaled air flow path 31 of the ventilation member 30 through the first flow path 42 of the relay member 40 (see an arrow G in FIG. 12). Accordingly, carbon dioxide in the exhaled air of the subject flowing in the exhaled flow path 31 is measured by the exhaled air sensor 13 supported by the ventilation member 30.

The exhaled air introduced into the exhaled air flow path 31 turns back at an end of the exhaled flow path 31 (see an arrow H in FIG. 12), passing through the second flow path 48 of the relay member 40 and returns to the internal space S inside the mask body portion 20 (see an arrow I in FIG. 12).

Part of the air inside the internal space S formed by the mask body portion 20 flows out from the holes 24 formed in the mask body portion 20 to the outside.

As explained above, the mask 10 according to the present embodiment includes the nasal cup 50 having the first wall portion 51 covering the nose N of the subject and the second wall portion 52 arranged under nostrils of the subject, therefore, it is possible to suppress that the exhaled air from the nose N of the subject is diluted by oxygen flowing from the inlet 11 of the mask 10 by the first wall portion 51 and the second wall portion 52 of the nasal cup 50. At least part of the exhaled air from the nose N of the subject is guided toward the exhaled air discharge portion 61 by the second wall portion 52, therefore, the exhaled air can be positively guided to the detection space 16 of the exhaled air sensor 13 even when a nasal tube having a high load for the subject is not used. As described above, the mask 10 is capable of reducing the load of the subject while suppressing lowering of the accuracy at which the exhaled air of the subject is measured can be provided according to the above structure.

As directly inserting the nasal tube into the nose N of the subject is not necessary, the load of the subject and also the number of components may be reduced. Therefore, attachment work may be simplified and costs may be reduced.

According to the above, the exhaled air of the subject can be smoothly guided to the exhaled air sensor 13 arranged outside the internal space S formed by the mask body portion 20 and can be accurately measured by the exhaled air sensor 13.

Additionally, the nasal cup 50 is integrally formed with the mouth cup 70 into which the exhaled air from the mouth M of the subject is introduced, and the internal spaces of the nasal cup 50 and the mouth cup 70 are partitioned by the second wall portion 52, therefore, the exhaled airs from the nose N and the mouth M can be positively guided to the exhaled air sensor 13 respectively through the exhaled air discharge portion 61.

The exhaled air of the nose N and the exhaled air of the mouth M may be joined after passing through the exhaled air discharge portion 61, and may be joined inside the exhaled air discharge portion 61 or before passing through the exhaled air discharge portion 61 by adjusting the height position of the second wall portion 52.

As the position of the nasal cup 50 with respect to the mask body portion 20 can be adjusted in the internal space S, the position of the nasal cup 50 with respect to the subject can be adjusted, and the exhaled air from the nose N of the subject can be guided to the exhaled air discharge portion 61 further positively.

The nasal cup 50 further includes the fitting portions 65 whereby the nasal cup 50 is attached to the mask body portion 20. The fitting portions 65 may be elongated and contracted, and thus facilitate attaching the nasal cup 50 to the subject.

In particular, the fitting portions 65 can be elongated and contracted easily by the elongation/contraction portions 66 having the bellows shape, therefore, the position of the nasal cup 50 can be easily adjusted and work of attaching the nasal cup 50 to the subject can be easily performed.

Furthermore, the exhaled air discharged from the exhaled air discharge portion 61 can be positively guided to the detection space 16 of the exhaled air sensor 13 by the ventilation member 30 connected to the opening 25 of the mask body portion 20.

In particular, the ventilation member 30 is attachable/detachable with respect to the opening 25 of the mask body portion 20, therefore, the ventilation member 30 of the mask 10 can be a disposable (throwaway) item.

The exhaled air sensor 13 is supported by the supporting portion 33 of the ventilation member 30, thereby measuring a state of the exhaled air of the subject in the state where the exhaled air sensor 13 is attached to the ventilation member 30.

Moreover, the relay member 40 connects the exhaled air discharge portion 61 and the ventilation member 30 and provides the flow path through which the exhaled air of the subject passes. Therefore, the exhaled air of the subject can be positively guided from the nasal cup 50 to the ventilation member 30 through the relay member 40.

As the flow path of the relay member 40 includes the first flow path 42 through which the exhaled air of the subject flows from the exhaled air discharge portion 61 toward the ventilation member 30 and the second flow path 48 through which the exhaled air of the subject flows from the ventilation member 30 toward the internal space S, the exhaled air guided to the ventilation member 30 through the first flow path 42 can flow into the internal space S of the mask body portion 20 through the second flow path 48, and the flow path to the ventilation member 30 opens to the internal space S of the mask body portion 20. Accordingly, the exhaled air of the subject easily flows to the ventilation member as compared with the case of the structure in which an exit of the flow path of the ventilation member 30 is blocked, as a result, the exhaled air of the subject can be measured with high accuracy.

Furthermore, the first flow path 42 and the second flow path 48 are arranged in parallel to each other, and the exhaled air flows in opposite directions to each other, therefore, the relay member 40 can be formed by a small-sized component.

The relay member 40 having the cylindrical portion 41 demarcating the first flow path 42 and the relay wall portion 47 formed at part of the opening of the cylindrical portion 41 and extending in an axial direction of the cylindrical portion 41 demarcates between the first flow path 42 and the second flow path 48 inside the ventilation member 30 in the state where the relay member 40 is attached to the ventilation member 30. Accordingly, the exhaled air of the subject flows to the ventilation member 30 easily and the exhaled air of the subject can be easily measured with high accuracy.

The mask body portion 20 includes the covering portion 21 covering the nose N and the mouth NI of the subject and the attachment portion 22 formed integrally with the covering portion 21 and can be elastically deformed. Accordingly, it is possible to accurately measure the exhaled air of the subject under the positive pressure ventilation and to reduce the load of the subject at the time of wearing the mask 10 by the elastically deformable attachment portion 22.

Furthermore, the holes 24 are provided in the covering portion 21 of the mask body portion 20, therefore, it is possible to suppress occurrence of a rebreathing state by the internal space S of the mask 10 being filled with the exhaled air of the subject.

Though the exhaled air sensor 13 that measures a carbon dioxide concentration of the exhaled air is provided in the embodiment, it goes without saying that measurement targets of the exhaled air include not only the concentration of a gas such as carbon dioxide but also a temperature of the exhaled air and so on.

Also, the case where the small-sized exhaled air sensor 13 attachable to the ventilation member 30 is provided is cited in the above embodiment, it is also preferable to adopt a structure where a pipe connected to the ventilation member 30 is provided and the exhaled air of the subject is fed into the exhaled air sensor 13 formed of a large stationary measuring instrument. It is also preferable to adopt a structure where the exhaled air sensor 13 is arranged inside the internal space S.

Second Embodiment

Next, a mask 10A according to a second embodiment of the present disclosure will be explained. In the first embodiment, the opening 25 to which the ventilation member 30 is connected and the inlet 11 to which the oxygen supply pipe 12 is connected are separately provided in the mask body portion 20 (see FIG. 3). The mask 10A according to the second embodiment is configured so that the oxygen supply pipe 12 and the ventilation member 30 can be attached to one opening 25A through a joint member 80. Hereinafter, the same symbols are added to members having the same functions as those in the first embodiment and explanation is omitted.

Figure 13:
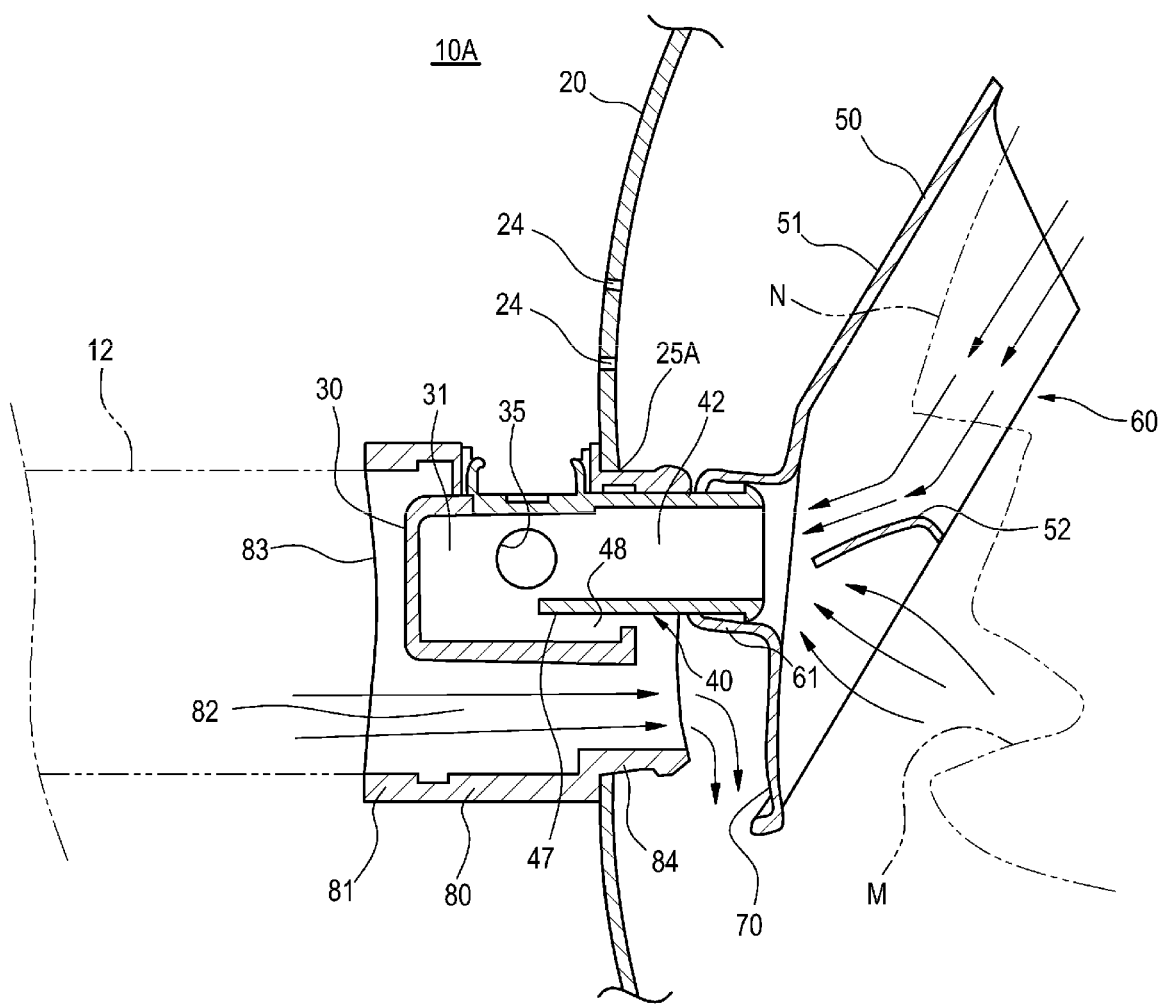
FIG. 13 is a cross-sectional view of a mask according to a second embodiment of the present disclosure.
Figure 14:
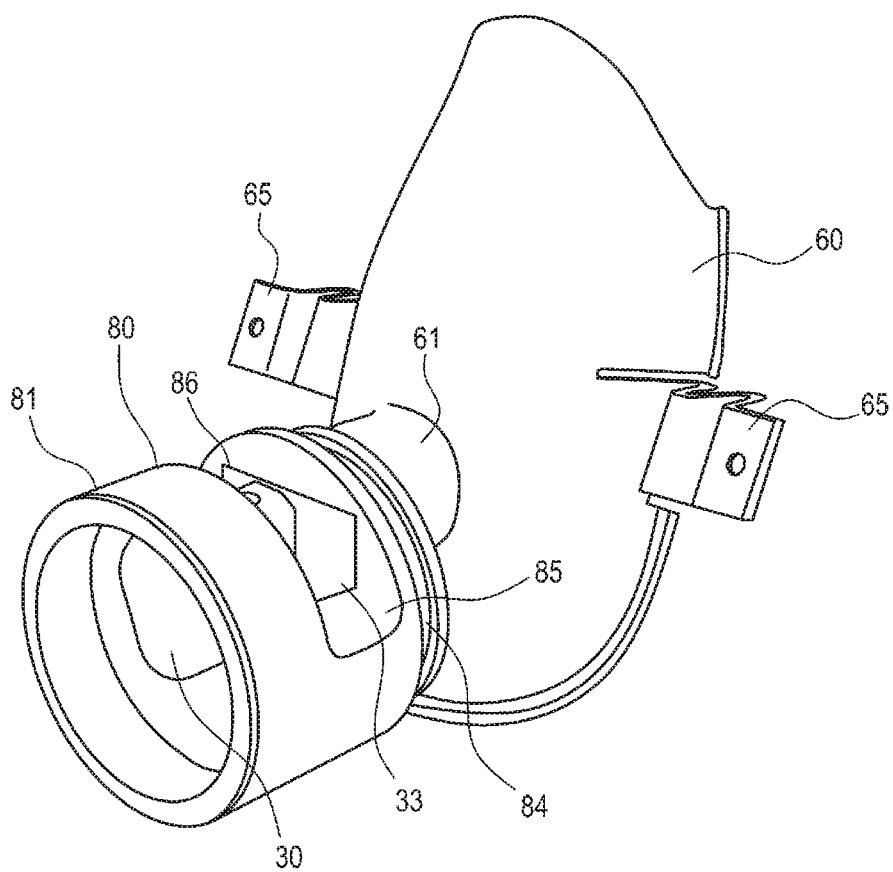
FIG. 14 is a perspective view seen from the front side of an exhaled air collection cup.

As shown in FIG. 13 and FIG. 14, the joint member 80 is fitted to the opening 25 of the mask 10A according to the second embodiment. The joint member 80 has a cylindrical portion 81 formed in a cylindrical shape, and the inside of the cylindrical portion 81 is made to be a flow path 82 of oxygen. One end side of the cylindrical portion 81 is a first connecting portion 83 connected to the oxygen supply pipe 12 and the other end side thereof is a second connecting portion 84 fitted and connected to the opening 25A.

A concave portion 85 for supporting the exhaled air sensor 13 is formed at part of the cylindrical portion 81. A concave portion 86 into which the ventilation member 30 can be fitted is formed at part of a wall surface forming the concave portion 85. The ventilation member 30 is supported by the joint member 80 in a state of being fitted into the concave portion 86. In the state where the ventilation member 30 is fitted to the joint member 80, the support portion 33 of the ventilation member 30 and the concave portion 85 of the joint member 80 function in conjunction with each other as parts supporting the exhaled air sensor 13.

When the joint member 80 into which the ventilation member 30 is fitted into the opening 25A from the outside of the mask body portion 20, and the relay member 40 connected to the exhaled air collection cup 60 is fitted into the ventilation member 30 from the inside of the mask body portion 20, a state shown in FIG. 13 can be obtained.

According to the above structure, the nasal cup 50 including the first wall portion 51 covering the nose N of the subject and the second wall portion 52 arranged under nostrils of the subject is provided, therefore, it is possible to suppress that the exhaled air from the nose N of the subject is diluted by oxygen flowing from the opening 25A of the mask 10A by the first wall portion 51 and the second wall portion 52 of the nasal cup 50. At least part of the exhaled air from the nose N of the subject is guided toward the exhaled air discharge portion 61 by the second wall portion 52, therefore, the exhaled air can be positively guided to the detection space 16 of the exhaled air sensor 13 even when a nasal tube having a high load for the subject is not used. As described above, the mask 10A capable of reducing the load for the subject while suppressing lowering of the accuracy at which the exhaled air of the subject is measured can be provided according to the above structure.

As it is possible to attach the oxygen supply pipe 12 and the ventilation member 30 to one opening 25A through the joint member 80, therefore, simplification and cost reduction in attachment work can be realized.

Third Embodiment

Next, a mask 10B according to a third embodiment of the present disclosure will be explained. The third embodiment differs from the second embodiment in a point that a mouth cup is not provided at an exhaled air collection cup 60A in the mask 10B according to the third embodiment.

Figure 15:
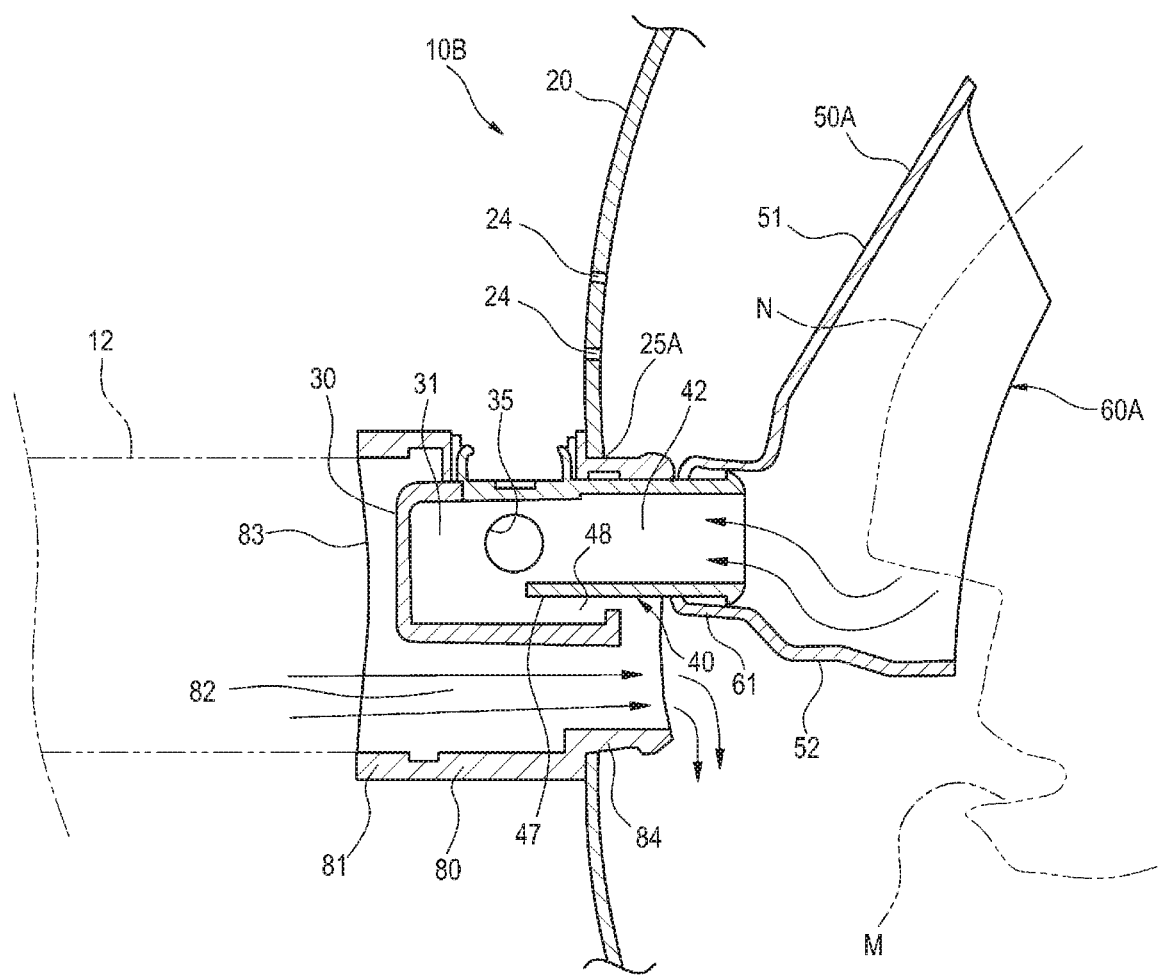
FIG. 15 is a cross-sectional view of a mask according to a third embodiment of the present disclosure.

As shown in FIG. 15, a nasal cup 50A forming the exhaled air collection cup 60A includes the first wall portion 51 covering the nose N of the subject and the second wall portion 52 arranged under nostrils of the subject. The first wall portion 51 is formed in a concave shape expanding to the front. The nasal cup 50A is arranged with a gap so that an upper part does not closely contact the nose N of the subject. The nasal cup 50A may have a shape closely contacting the nose of the subject.

The exhaled air collection cup 60A has the exhaled air discharge portion 61. The exhaled air discharge portion 61 is formed integrally with the first wall portion 51, and is formed in a cylindrical shape protruding to the front. The exhaled air from the nose N of the subject is guided to the front of the exhaled air discharge portion 61 by the second wall portion 52 and fed into the exhaled air discharge portion 61.

According to the above structure, the nasal cup 50A including the first wall portion 51 covering the nose N of the subject and the second wall portion 52 arranged under nostrils of the subject is provided, therefore, it is possible to suppress that the exhaled air from the nose N of the subject is diluted by oxygen flowing from the opening 25A of the mask 10B into the inside of the mask 10B by the first wall portion 51 and the second wall portion 52 of the nasal cup 50A. Moreover, the oxygen supply pipe 12 and the ventilation member 30 can be attached to one opening 25A through the joint member 80, therefore, simplification and cost reduction in attachment work can be realized.

Modification Example 1

Figure 16:
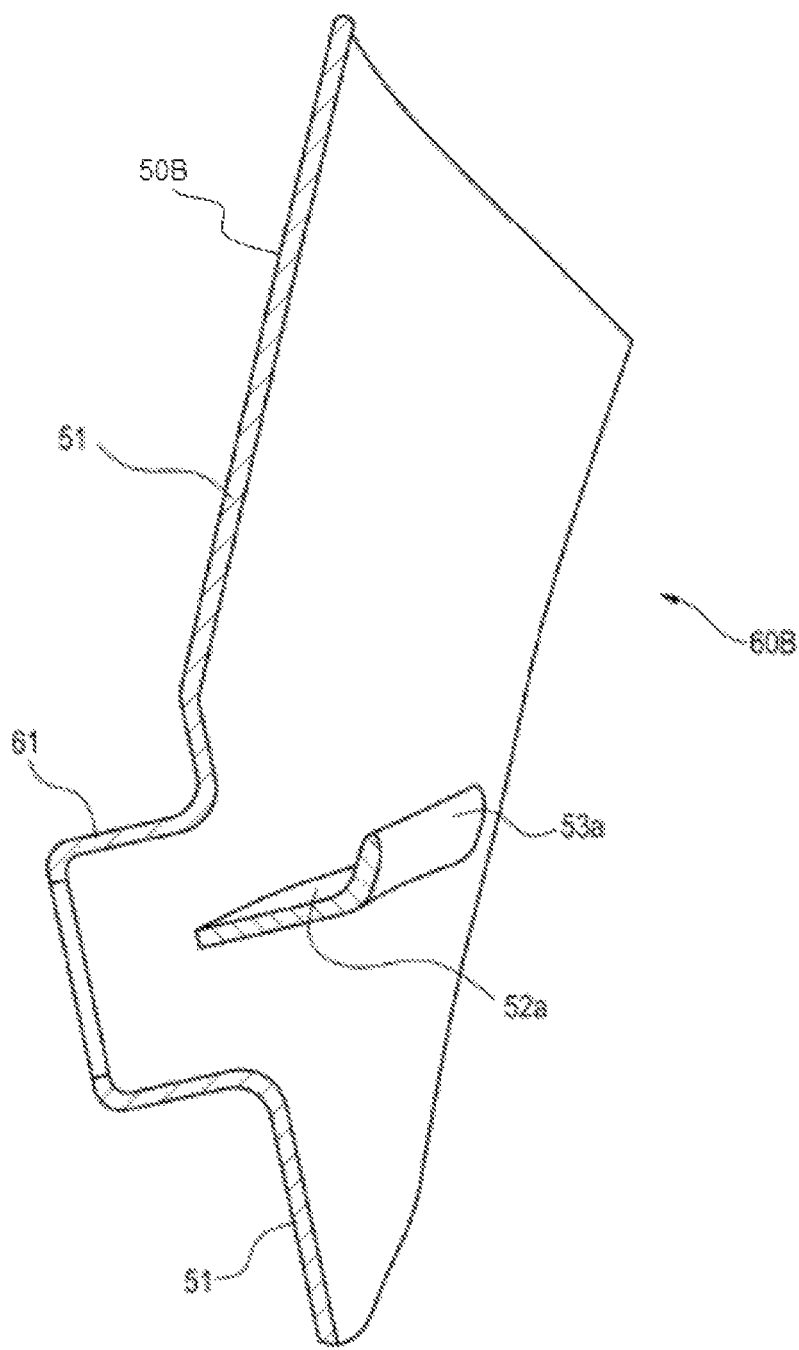
FIG. 16 is a cross-sectional view of an exhaled air collection cup according to a modification example 1.
Figure 17:
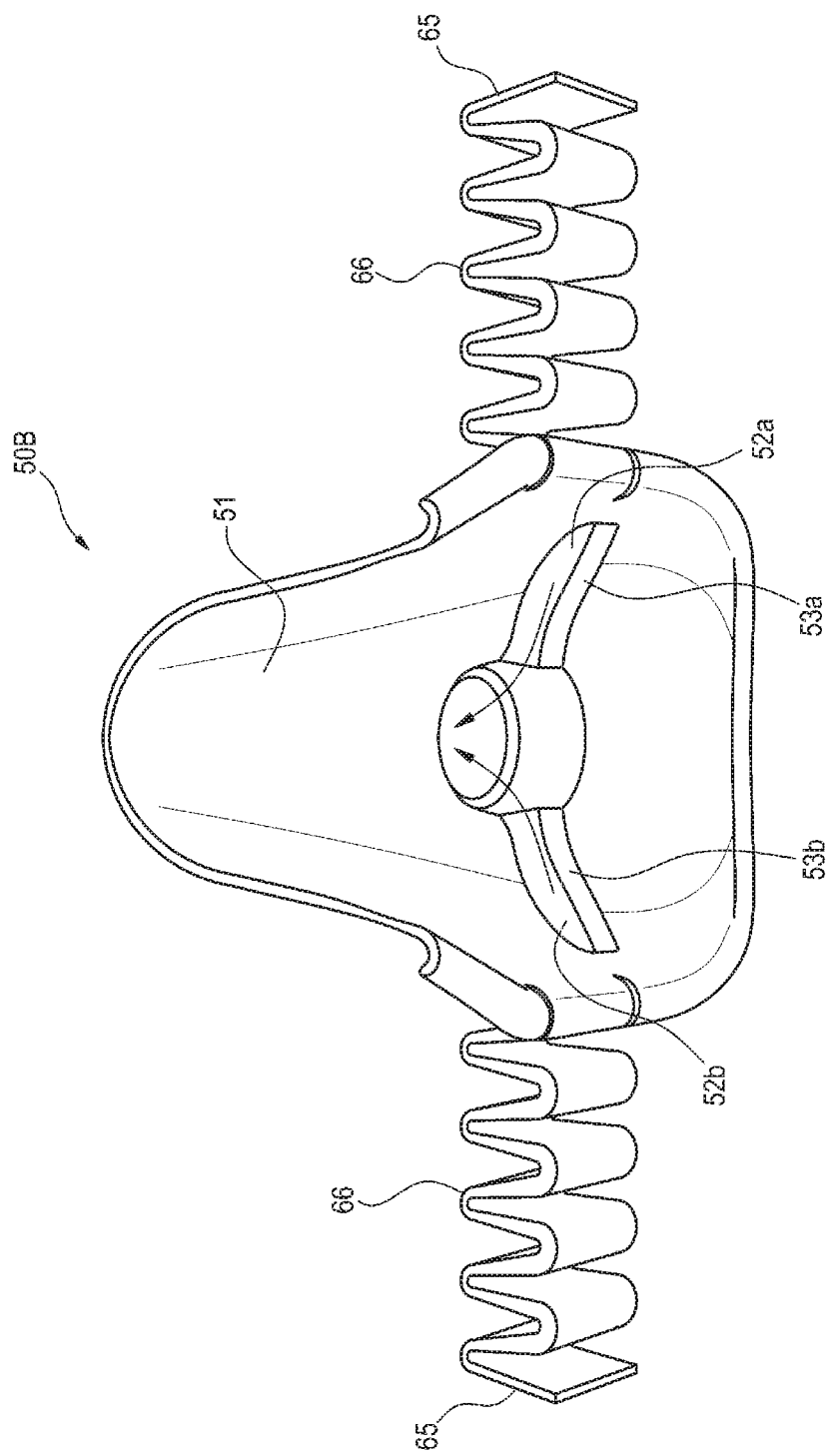
FIG. 17 is a view of the exhaled air collection cup according to the modification example 1 seen from above.

FIG. 16 and FIG. 17 show a modification example 1 of the exhaled air collection cup. FIG. 16 is a vertical cross-sectional view of an exhaled air collection cup 60B. FIG. 17 is a view of the exhaled air collection cup 60B seen from above. The exhaled air collection cup 60B shown in FIG. 16 and FIG. 17 differs from the exhaled air collection cup 60 shown in FIG. 4 to FIG. 6 in the shape of the second wall portion 52.

In a nasal cup 50B forming the exhaled air collection cup 60B, the second wall portion 52 is formed separately into a second wall portion 52a for a right nostril and a second wall portion 52b for a left nostril (see FIG. 17). The second wall portion 52a for the right nostril and the second wall portion 52b for the left nostril are arranged right and left separately so as to be centered on the exhaled air discharge portion 61.

The second wall portion 52a for the right nostril is curved upward at an end portion 53a farther from the exhaled air discharge portion 61. The second wall portion 52b for the left nostril is curved upward at an end portion 53b farther from the exhaled air discharge portion 61.

According to the structure of the exhaled air collection cup 60B, an exhaled air from the right nostril of the subject is guided to the exhaled air discharge portion 61 by the second wall portion 52a and an exhaled air from the left nostril is guided toward the exhaled air discharge portion 61 by the second wall portion 52b, and these exhaled airs are joined in the vicinity of the center of an entrance of the opening of the exhaled air discharge portion 61 and flow toward an exit. As a result, the exhaled air of the subject easily flows to the detection space 16 of the exhaled air sensor 13 and the exhaled air of the subject can be easily measured accurately.

Modification Example 2

Figure 18:
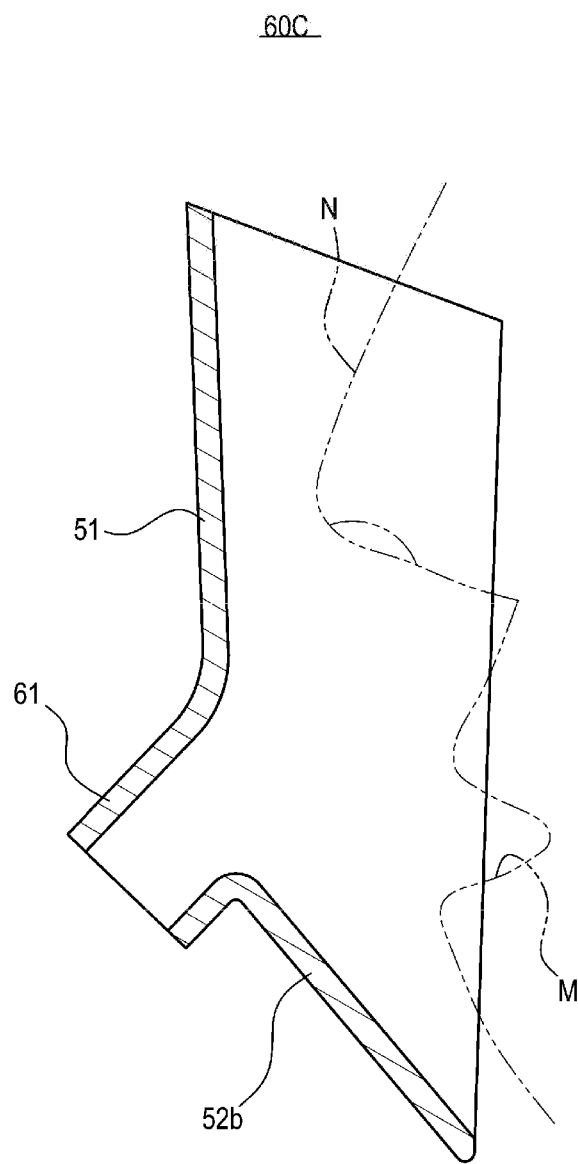
FIG. 18 is a cross-sectional view of an exhaled air collection cup according to a modification example 2.

FIG. 18 shows a modification example 2 of the exhaled air collection cup. An exhaled air collection cup 60C shown in FIG. 18 includes the first wall portion 51 covering the nose N of the subject, the second wall portion 52b arranged under nostrils of the subject as well as in front of the mouth M of the subject and the exhaled air discharge portion 61. The exhaled air discharge portion 61 is arranged between the first wall portion 51 and the second wall portion 52b, which is formed integrally with them in a cylindrical shape protruding in a front and lower directions. At least part of the exhaled air from the nose N of the subject is guided by the second wall portion 52b and fed into the exhaled air discharge portion 61. At least part of the exhaled air from the mouth M of the subject is guided by the second wall portion 52b and fed into the exhaled air discharge portion 61. Also according to the structure, the same operations and effects as the above embodiments and modification examples can be obtained.

The present disclosure is not limited to the above embodiments, and may be appropriately modified and improved freely. Additionally, the material, shape, size, numeral, state, number, arrangement place and the like of respective components in the above embodiments are arbitrary and not limited as long as the present disclosure can be achieved.

For example, the mask explained in the above examples may be adopted to a system measuring a carbon dioxide concentration in the exhaled air in a side stream system. For example, it is possible to adopt a structure in which a sampling tube connected to a gas measuring device (not shown) is connected to members (the nasal cup 50, the mouth cup 70, the exhaled air discharge portion 61, the relay member 40, the ventilation member 30 and so on) having paths through which the exhaled air passes to thereby guide the exhaled air to the gas measuring device through these members and the sampling tube.

What is claimed is:

1. A mask configured to be put on a face of a subject, comprising: a mask body portion demarcating an internal space, wherein the mask body portion is adapted to cover part of the face of the subject; and a cup-shaped nasal cup adapted to cover a nose of the subject, wherein the nasal cup is arranged inside the internal space, wherein the nasal cup includes a first wall portion adapted to cover the nose of the subject, a second wall portion adapted to be arranged under nostrils of the subject, and an exhaled air discharge portion adapted to guide an exhaled air from the nose of the subject to an exhaled air sensor, whereby at least part of the exhaled air from the nose of the subject is guided toward the exhaled air discharge portion by the second wall portion in a state where the nasal cup is adapted to cover the nose of the subject, wherein the exhaled air discharge portion is integrally formed with the first wall portion, wherein the exhaled air discharge portion extends from the first wall portion toward the mask body portion in a direction away from the face of the subject, wherein the second wall portion includes a surface adapted to face the nostrils from below without the second wall portion being inserted into the nostrils, the surface extending toward the exhaled air discharge portion, and the second wall portion extends in the direction away from the face of the subject, and wherein the second wall portion is spaced apart from the exhaled air discharge portion with an upper space and a lower spaces between the second wall portion and the exhaled air discharge portion.

2. The mask according to claim 1,
wherein the exhaled air discharge portion is connected to an opening provided in the mask body portion adapted to guide the exhaled air from the nose of the subject to the exhaled air sensor arranged outside the internal space.

3. The mask according to claim 1,
whereby the nasal cup is formed integrally with a mouth cup into which an exhaled air from a mouth of the subject is introduced,
the nasal cup and the mouth cup are partitioned into respective internal spaces by the second wall portion, and
the exhaled air discharge portion is capable of guiding the exhaled air from the nose of the subject and the exhaled air from the mouth of the subject to the exhaled air sensor arranged outside the internal space.

4. The mask according to claim 1,
wherein the nasal cup is capable of adjusting a position inside the internal space with respect to the mask body portion.

5. The mask according to claim 1,
wherein the nasal cup has fitting portions capable of being fitted to the mask body portion, and
the fitting portions are capable of being elongated or contracted.

6. The mask according to claim 5,
wherein the fitting portions have bellows-shaped portions.

7. The mask according to claim 2, further comprising:
a ventilation member guiding the exhaled air discharged from the exhaled air discharge portion to a detection space of the exhaled air sensor,
wherein the ventilation member is connected to the opening of the mask body portion.

8. The mask according to claim 7,
wherein the ventilation member is attachable/detachable with respect to the opening of the mask body portion.

9. The mask according to claim 7,
wherein the ventilation member has a supporting portion that supports the exhaled air sensor.

10. The mask according to claim 7, further comprising:
a relay member connecting between the exhaled air discharge portion and the ventilation member and whereby having a flow path through which the exhaled air of the subject passes.

11. The mask according to claim 10,
whereby the flow path includes
a first flow path through which the exhaled air of the subject flows from the exhaled air discharge portion toward the ventilation member, and
a second flow path through which the exhaled air of the subject flows from the ventilation member toward the internal space.

12. The mask according to claim 11,
wherein the first flow path and the second flow path are arranged in parallel to each other, and
the first flow path and the second flow path flow in opposite directions to each other.

13. The mask according to claim 11,
wherein the relay member includes
a cylindrical portion demarcating the first flow path, and
a relay wall portion formed at part of an opening of the cylindrical portion and extending in an axial direction of the cylindrical portion, and
the relay wall portion demarcates between the first flow path and the second flow path inside the ventilation member in a state where the relay member is attached to the ventilation member.

14. The mask according to claim 1,
wherein at least one or more holes are provided in a covering portion.

15. The mask according to claim 1,
wherein the second wall portion is configured so that a portion adapted to be arranged under a right nostril of the subject and a portion adapted to be arranged under a left nostril of the subject are formed separately.

16. The mask according to claim 1,
wherein at least one of the nasal cup, a mouth cup, the exhaled air discharge portion, a relay member and a ventilation member is connected to a gas measuring device through a sampling tube, wherein the at least one of the nasal cup, the mouth cup, the exhaled air discharge portion, the relay member, and the ventilation member is configured to provide the exhaled air to the gas measuring device.

17. The mask according to claim 1,
wherein the exhaled air discharge portion has a first engagement portion that is engaged with a second engagement portion of a relay member configured to discharge the exhaled air from the exhaled air discharge portion and guide the exhaled air to the exhaled air sensor.

18. The mask according to claim 1, wherein the exhaled air discharge portion is adapted to be arranged in front of the face of the subject when the mask is adapted to be put on the face of the subject.

19. The mask according to claim 1, wherein the mask body portion includes:
a covering portion adapted to cover a nose and a mouth of the subject, and
an attachment portion formed integrally with the covering portion and is capable of being elastically deformed.

20. The mask according to claim 1, wherein the at least part of the exhaled air from the nose of the subject is guided toward the exhaled air discharge portion through the upper space between the second wall portion and the exhaled air discharge portion, and at least part of an exhaled air from a mouth of the subject is guided toward the exhaled air discharge portion through the lower space between the second wall portion and the exhaled air discharge portion.

21. A mask configured to be put on a face of a subject, comprising:
a mask body portion demarcating an internal space, wherein the mask body portion is adapted to cover part of the face of the subject; a cup-shaped nasal cup adapted to cover a nose of the subject, wherein the nasal cup is arranged inside the internal space; wherein the nasal cup includes a first wall portion adapted to cover the nose of the subject, a second wall portion adapted to be arranged under nostrils of the subject, and an exhaled air discharge portion adapted to guide an exhaled air from the nose of the subject to an exhaled air sensor, whereby at least part of the exhaled air from the nose of the subject is guided toward the exhaled air discharge portion by the second wall portion in a state where the nasal cup is adapted to cover the nose of the subject, wherein the exhaled air discharge portion is integrally formed with the first wall portion, wherein the exhaled air discharge portion extends from the first wall portion toward the mask body portion in a direction away from the face of the subject, wherein the second wall portion includes a surface adapted to face the nostrils from below without the second wall portion being into the nostrils, the surface extending toward the exhaled air discharge portion, and the second wall portion extends in the direction away from the face of the subject, and a ventilation member guiding the exhaled air discharged from the exhaled air discharge portion to a detection space of the exhaled air sensor; and a relay member connecting between the exhaled air discharge portion and the ventilation member and whereby having a flow path through which the exhaled air of the subject passes, wherein the flow path includes a first flow path through which the exhaled air of the subject flows from the exhaled air discharge portion toward the ventilation member, and a second flow path through which the exhaled air of the subject flows from the ventilation member toward the internal space.

22. The mask according to claim 21, wherein the exhaled air discharge portion and an oxygen supply pipe are connected to an opening provided in the mask body portion.

23. The mask according to claim 22, wherein the oxygen supply pipe is connected to the opening through a cylindrical joint member, and the ventilation member is arranged inside the joint member.

24. An exhaled air collection cup, comprising:
a first wall portion adapted to cover a nose of a subject,
a second wall portion adapted to be arranged under nostrils of the subject, and
an exhaled air discharge portion adapted to guide an exhaled air from the nose of the subject to an exhaled air sensor,
wherein the exhaled air discharge portion is formed integrally with the first wall portion,
wherein the exhaled air discharge portion extends from the first wall portion towards a mask body portion in a direction away from a face of the subject,
wherein the second wall portion includes a surface adapted to face the nostrils from below, the surface extending toward the exhaled air discharge portion,
wherein the second wall portion is configured so that a portion is adapted to be arranged under a right nostril of the subject and a portion is adapted to be arranged under a left nostril of the subject are formed separately without the second wall portion being inserted into the left nostril or the right nostril, and
wherein at least part of the exhaled air from the nose of the subject is guided toward the exhaled air discharge portion by the second wall portion.

25. A mask configured to be put on a face of a subject, comprising:
a mask body portion demarcating an internal space, wherein the mask body portion is adapted to cover part of the face of the subject; and a cup-shaped nasal cup adapted to cover a nose of the subject, wherein the nasal cup is arranged inside the internal space, wherein the nasal cup includes: a first wall portion adapted to cover the nose of the subject, a second wall portion adapted to be arranged under nostrils of the subject, and an exhaled air discharge portion adapted to guide an exhaled air from the nose of the subject to an exhaled air sensor, whereby at least part of the exhaled air from the nose of the subject is guided toward the exhaled air discharge portion by the second wall portion in a state where the nasal cup is adapted to cover the nose of the subject, wherein the exhaled air discharge portion is adapted to protrude to a front of the subject in front of the first wall, wherein the second wall portion includes a surface adapted to face the nostrils from below without the second wall portion being inserted into the nostrils, the surface extending toward the exhaled air discharge portion, and the second wall portion extends in a direction away from the face of the subject, and wherein the exhaled air discharge portion is configured to extend diagonally downward in a direction along a ridge of the nose.

26. The mask according to claim 25, wherein the exhaled air discharge portion is adapted to be arranged in front of the face of the subject when the mask is adapted to be put on the face of the subject.

27. The mask according to claim 25, wherein the mask body portion includes:
a covering portion configured to cover a nose and a mouth of the subject, and
an attachment portion formed integrally with the covering portion and is capable of being elastically deformed.

* * * * *